US008715187B2

(12) United States Patent
Landberg Davis et al.

(10) Patent No.: US 8,715,187 B2
(45) Date of Patent: May 6, 2014

(54) SYSTEMS AND METHODS FOR AUTOMATICALLY IDENTIFYING AND SEGMENTING DIFFERENT TISSUE TYPES IN ULTRASOUND IMAGES

(75) Inventors: Cynthia Elizabeth Landberg Davis, Niskayuna, NY (US); Ying Fan, Niskayuna, NY (US); Hae Won Lim, Niskayuna, NY (US); Gokul Swamy, Bangalore (IN); Navneeth Subramanian, Bangalore (IN); Nitya Subramaniam, Bangalore (IN)

(73) Assignee: General Electric Company, Niskayuna, NY (US)

( * ) Notice: Subject to any disclaimer, the term of this patent is extended or adjusted under 35 U.S.C. 154(b) by 349 days.

(21) Appl. No.: 12/971,241

(22) Filed: Dec. 17, 2010

(65) Prior Publication Data
US 2012/0157842 A1    Jun. 21, 2012

(51) Int. Cl.
*A61B 8/08*    (2006.01)
(52) U.S. Cl.
USPC ............................... 600/439; 600/443; 601/2
(58) Field of Classification Search
USPC ..................... 600/437, 439; 601/2; 604/22
See application file for complete search history.

(56) References Cited

U.S. PATENT DOCUMENTS

| 6,071,239 | A | 6/2000 | Cribbs et al. |
| 7,258,674 | B2 | 8/2007 | Cribbs et al. |
| 2008/0015435 | A1* | 1/2008 | Cribbs et al. ............... 600/437 |
| 2008/0306476 | A1 | 12/2008 | Hennings et al. |
| 2010/0036246 | A1 | 2/2010 | Kushculey et al. |
| 2010/0081971 | A1 | 4/2010 | Allison et al. |
| 2010/0160781 | A1* | 6/2010 | Carter et al. ............... 600/439 |

OTHER PUBLICATIONS

Darren D. Brennan et al; "Rapid Automated Measurement of Body Fat Distribution from Whole Body MRI"; American Journal of Roentgenology, vol. 185, Issue 2, Aug. 2005; 12Pages.

* cited by examiner

*Primary Examiner* — Parikha Mehta
(74) *Attorney, Agent, or Firm* — Jenifer E. Haeckl

(57) ABSTRACT

A system for providing non-invasive ultrasound based treatment to a region of interest is provided. The system comprises an imaging unit for imaging one or more tissue types in the region of interest, an image processing unit that is configured to identify the one or more tissue types in the region of interest, an ultrasound transducer that is configured to focus an ultrasound beam to ablate at least a portion of the identified tissues, and a controller unit that controls a delivery of the ultrasound beam to the region of interest.

22 Claims, 7 Drawing Sheets

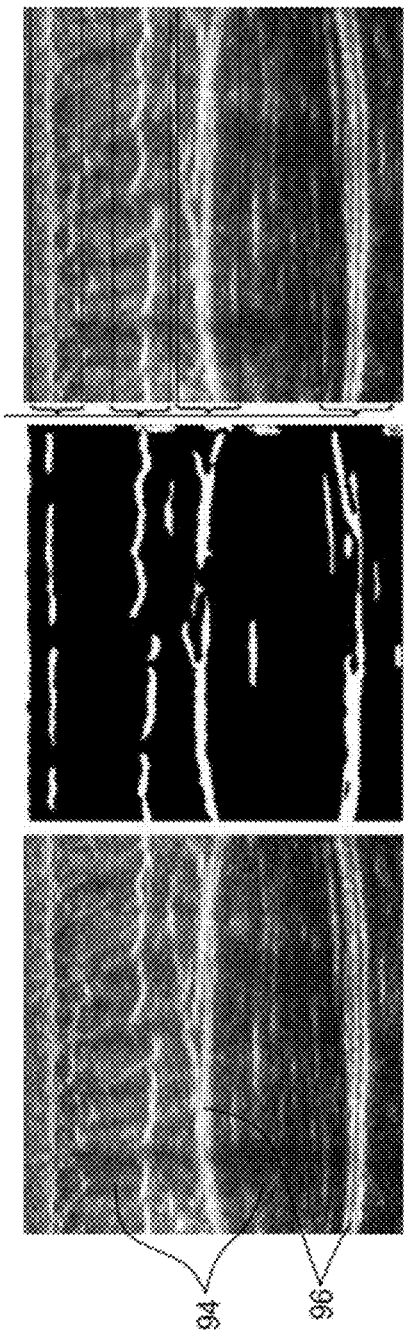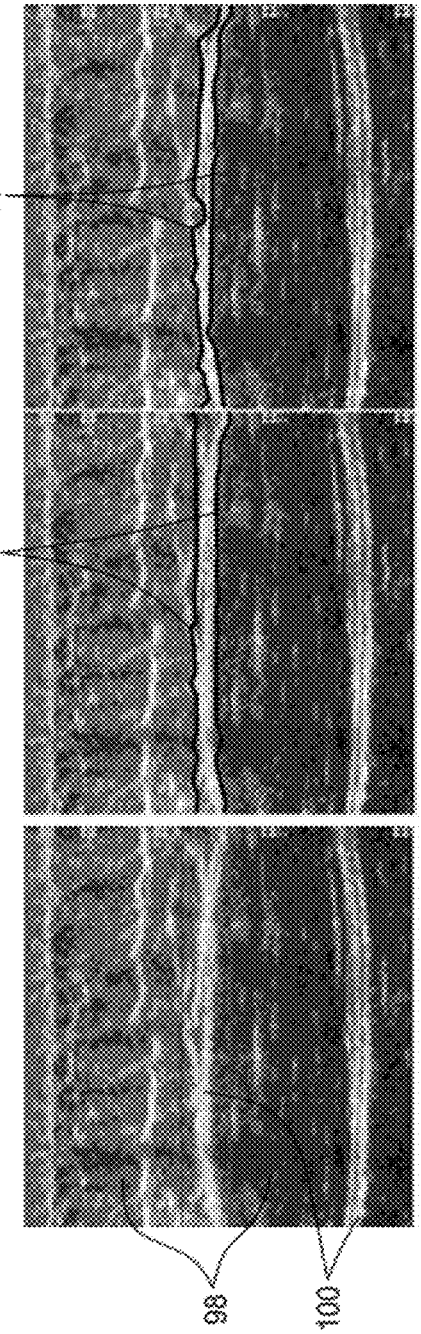

SYSTEMS AND METHODS FOR AUTOMATICALLY IDENTIFYING AND SEGMENTING DIFFERENT TISSUE TYPES IN ULTRASOUND IMAGES

BACKGROUND

The invention relates to treatment of tissues, and more particularly to methods and systems for treatment of tissues using ultrasound.

Undesirable tissues such as subcutaneous fat, visceral fat, lipomas and tumors may be non-invasively treated using ultrasound. Typically, focused ultrasound with a thermal or cavitational treatment is used for treatment of such tissues. In a thermal treatment, the ultrasound power is concentrated for a short continuous duration and the tissue is heated by intense vibrations. In a cavitational treatment, ultrasound energy is used to vibrate the tissues in a relatively less intense manner in order to damage the cells. The damaged cells may subsequently die via a necrotic or apoptotic cell death. During ablation, damage to the tissues may be achieved via a combination of thermal and cavitational effects by adjustment of the ultrasound parameters by carefully selecting the ultrasound transducer frequency. For example, a transducer with a frequency range from about 1 MHz to about 2 MHz may be adjusted to run in a low duty cycle pulsed mode for a predominantly cavitational effect. However, if the duty cycle is increased to a continuous wave (CW) the effect may be predominantly thermal.

The cavitation threshold for various tissues is different. Hence, for a cavitational treatment it is desirable to determine the tissue types that are to be treated and adjust the treatment accordingly. For example, in case of cosmetic ablation of adipose tissue, it is desirable to have a precise determination of the location of fat layer. A precise determination of the location of the tissues is required for locating the fat layer for ablation as well as for post ablative examination of the residual layer.

Therefore, it would be desirable to provide a method for automatically identifying and segmenting different tissue types in ultrasound images for performing procedures, such as ablation.

BRIEF DESCRIPTION

In one embodiment, a system for providing non-invasive ultrasound based treatment to a region of interest is provided. The system comprises an imaging unit for imaging one or more tissue types in the region of interest, an image processing unit that is configured to identify the one or more tissue types in the region of interest, an ultrasound transducer that is configured to focus an ultrasound beam to ablate at least a portion of the identified tissues, and a controller unit that controls a delivery of the ultrasound beam to the region of interest.

In another embodiment, a method for treating a region of interest using ultrasound is provided. The method comprises acquiring ultrasound images of the region of interest, identifying one or more tissue types in the ultrasound images, segmenting the tissue types in the ultrasound images, identifying tissues to be ablated, focusing an ultrasound beam to ablate at least a portion of the identified tissues, and ablating the portion of the identified tissues.

DRAWINGS

These and other features, aspects, and advantages of the present invention will become better understood when the following detailed description is read with reference to the accompanying drawings in which like characters represent like parts throughout the drawings, wherein:

FIG. 4 is an example input ultrasound image for automatically identifying and segmenting tissue types in a region of interest;

FIGS. 5-6 are processed ultrasound images at different stages during application of methods of the invention to the input ultrasound image of FIG. 4 for automatically identifying and segmenting tissue types in the region of interest;

FIGS. 7-10 are processed ultrasound images after different iterations during application of algorithm for automatically identifying and segmenting tissue types in a region of interest;

DETAILED DESCRIPTION

Figure 1:
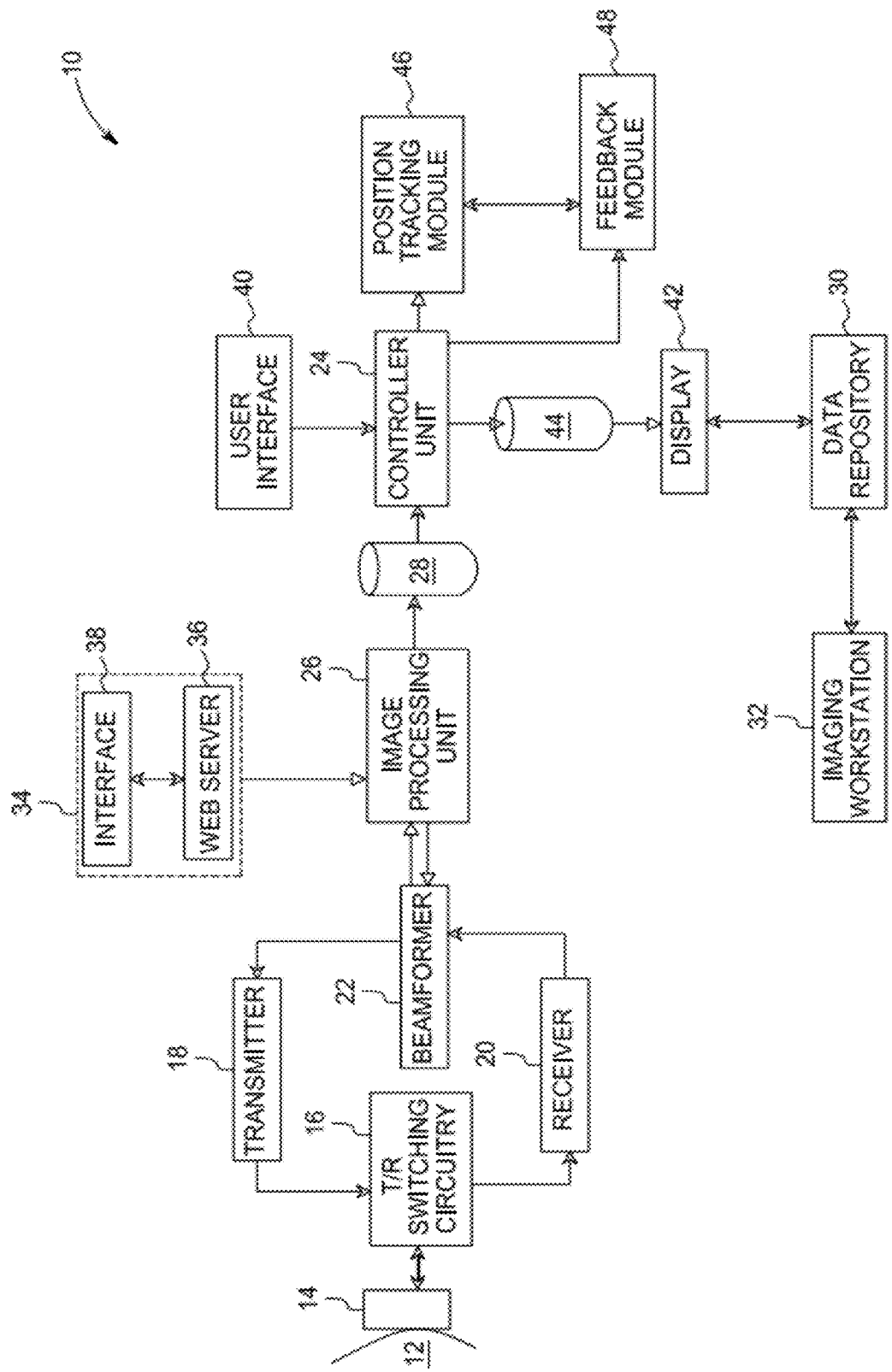
FIG. 1 is a schematic drawing of an example of an ultrasound system for automatically identifying and segmenting tissue types in a region of interest.

Embodiments of the invention relate to systems and methods for automatically treating tissues using ultrasound. Prior to or during the step of treating a region of interest, at least a portion of the region of interest is imaged and different tissue types are automatically identified and segmented in the acquired ultrasound images. Based on the identification and segmentation of the different tissue types, an optimized treatment is planned. For example, planning may comprise adjusting the ultrasound parameters (such as shape, size, location, or direction of the ultrasound beam) to maximize the treatment efficiency and minimize the damage to healthy tissues during the treatment. The treatment may be provided using high intensity focused ultrasound (HIFU).

In certain embodiments, the optimal treatment is planned based on the identification and segmentation of the fat tissues, vessels and connective tissues in the region of interest. In one embodiment, the connective tissue layers may be identified before the fat tissues or muscles. The identification of the different tissue types may be performed in several ways. For example, the identification may be performed based on the intensity of the backscattered reflection and/or the textural properties of the region. Additionally, prior to identification, the image features may be enhanced using any combination of image enhancing filters, such as but not limited to, vessel enhancing filters, coherence enhancing filters etc. In one example, where the region of interest comprises fat and muscle, the region may be segmented between any two adjacent connective tissue layers, and the tissue layers may be classified into one of two categories, namely fat and muscle. In one embodiment, the HIFU focal spot may be directed at the fat tissues and the connective tissues may be prevented from being damaged.

To more clearly and concisely describe the subject matter of the claimed invention, the following definitions are provided for specific terms, which are used in the following description and the appended claims. Throughout the specification, exemplification of specific terms should be considered as non-limiting examples.

As used herein, "cavitation" refers to treating tissue (such as fat tissue) primarily with cavitational mechanism. However, cavitation or cavitating may also have thermal effects on the tissue. The tissue may be destroyed either by cavitation or thermal effect. HIFU parameters may be adjusted such that the majority of the damage to tissue is cavitational in nature, but there may be thermal effects or damages to the tissue.

As used herein, "thermal treatment" refers to treating tissue primarily with a mechanism that is thermal in nature. However, thermally treating may have cavitational effects.

As used herein, "adipose tissue" means subcutaneous, visceral or other tissues made primarily of fat cells. Adipose tissues may also comprise connective tissues, blood vessels and other structures. Adipose tissue may be white adipose tissue or brown adipose tissue.

As used herein, "connective tissue" or "connective tissue layer" is found either in the adipose tissue or in the skin surrounding the adipose tissue.

As used herein, "patient" or "subject" means a person or living being receiving therapy using the ultrasound transducer assembly. The terms "patient" and "subject" may be used interchangeably throughout the application.

As used herein, "region of interest" means one or more sites associated with the patient targeted for receiving the therapy. The region of interest may or may not be imaged along with the therapy treatments. The region of interest may include, but is not limited to, an inner (deeper) treatment region such as visceral fat, a subcutaneous region of interest and/or any other region of interest in between the inner treatment region, and/or a subcutaneous region within a patient.

As used herein, "therapy transducer" refers to an ultrasound transducer that generates ultrasound energy for therapeutic purposes to be delivered to a region of interest.

As used herein, "user" means one or more persons (e.g. skilled technician or physician) operating at least part of the system to provide therapy to the patient.

In certain embodiments, the ultrasound system comprises an imaging unit for acquiring ultrasound images and an image processing unit for automatic analysis of the ultrasound images. In one example, low energy ultrasound may be used for acquiring images. The analysis of the ultrasound images is performed to identify and subsequently segment the various tissue types in the images. Based on the analysis, an optimal treatment may be planned. Planning the treatment may comprise determining ultrasound parameters, and determining location of the tissues that need to be treated as well as the location of the neighboring tissues that do not need to be treated. The ultrasound system comprises a controller unit that works in tandem with the image processing unit to deliver planned treatment to the region of interest based on the identification and segmentation of the tissue types. In one example, the controller unit may facilitate adjusting the location of the treatment area (focal spot) of the ultrasound transducer based on the tissue identification. The controller unit may be configured to adjust an ultrasound focal spot location in three dimensions. The location of the ultrasound focal spot may be adjusted either by a mechanical motion or an electronic adjustment. Optionally, the ultrasound system comprises a feedback control unit that may further adjust the focal spot. In one example, subsequent to low energy imaging of the region of interest, the focal spot may be further adjusted using the feedback control unit. Optionally, a cavitation detector may be used to detect the amount of cavitation. In one example, the imaging unit may be configured to operate as a cavitation detector. For example, if the imaging unit comprises an imaging ultrasound transducer, the imaging transducer may be configured to serve the dual purpose of the imaging transducer and a cavitation detector. In one embodiment, the feedback control unit may be used to adjust the ultrasound parameters once cavitation is detected. The ultrasound parameters may be adjusted to maintain cavitation in the area of treatment with minimal power usage to substantially reduce the probability of burns to the skin that may be otherwise caused due to thermal heating.

FIG. 1 is a block diagram of an example of an ultrasound system 10 for identifying and segmenting different tissue types in ultrasound images. The treatment may be planned based on the identification and segmentation of the tissue types. The ultrasound system 10 may be configured to non-invasively deliver therapy and/or to image a region of interest 12 via a probe housing. The region of interest 12 may be a three dimensional region. The region of interest 12, having diseased tissue or undesirable tissue, is located inside a patient. In one example, delivery of therapy may comprise destroying the diseased tissues or undesirable tissues in the region of interest 12 by heating or by inducing cavitation.

The probe housing comprises an integrated transducer 14 comprising a therapy transducer and an imaging transducer. The integrated transducer 14 comprising the imaging transducer and the therapy transducer may be disposed in the probe housing. Although the system 10 is described with respect to an integrated transducer 14, it should be noted that separate therapy and imaging transducers may be used in the system 10. In case of separate therapy and imaging transducers, one or both the transducers may be disposed in the probe housing. The integrated transducer 14 may be coupled to transmit/receive switching circuitry 16, a transmitter 18, and (optionally) a receiver 20. The receiver 20 is required for the imaging transducer of the integrated transducer 14. When the imaging transducer is used in conjunction with the therapy transducer, the receiver 20 may be used to acquire back-scattered acoustic energy from the region of interest for imaging purposes.

The imaging signals are back-scattered from physiological structures in the body, for example, adipose tissue, muscular tissue, blood cells, veins or objects within the body (e.g., a catheter or needle) to produce echoes that return to the imaging transducer. The imaging transducer may receive the back-scattered waves at different times, depending on the distance into the tissue they return from and the angle with respect to the surface of the imaging transducer at which they return. The transducer elements convert the ultrasound energy from the backscattered waves into electrical signals. The electrical signals are then routed through the T/R switching circuitry 16 to the receiver 20. The receiver 20 amplifies and digitizes the received signals and provides other functions such as gain compensation. The digitized received signals, corresponding to the backscattered waves, are received, in this example, by each transducer element at various times, and preserve the amplitude and phase information of the backscattered waves.

The backscattered signals or echoes are received by the receiver 20 for imaging purposes. The received echoes are provided to an image processing unit 26 that processes the signals. The processed data may be transmitted to the controller unit 24, a memory 28, or data repository 30 for temporary or permanent storage. The data repository 30 may be configured to receive data and interact with an imaging workstation 32. The processor 30 may be coupled to a remote connectivity subsystem 34 comprising a web server 36 and a remote connectivity interface 38. The image processing unit 26 is used for automatically identifying and segmenting the different tissue types in ultrasound images.

The therapy or imaging transducers may include one or more transducer elements, one or more matching layers, and focusing components, such as lens. The transducer elements may be arranged in a spaced relationship, such as, but not limited to, a one or two-dimensional transducer array, a phased array, or an annular array. The transducer 14 may allow for mechanical translation of the HIFU elements or electronic steering in the case of the phased array or annular array (in the z direction). The transducer 14 may employ a single channel or multiple channels for transmission.

In case of a phased array therapy transducer, the transducer elements may be connected to, and controlled by a controller unit 24. The controller unit 24 may be able to activate and control each element independently. By steering, or phasing the individual elements appropriately, a converging wavefront may be created. Alternatively, a mechanical lens may be disposed in front of a single element transducer to cause the phase delays. The phase array transducer may be used to obtain a different phase pattern, or a different focal point. The phased array may be used to steer and focus simultaneously. The annular array transducers may be used for larger depth of focus.

In certain embodiments, operation of the integrated transducer 14 is controlled using the controller unit 24. Specifically, the transducer 14 is operatively coupled to the controller unit 24 to control the parameters of the ultrasound beam. Non-limiting examples of the ultrasound parameters may include shape, size, location, or direction of the ultrasound beam. In one embodiment, the transducer or transducer elements may be moved along or about one or more of x, y or z directions to adjust the parameter of the ultrasound beam. For example, the transducer may be rotated about the z direction, or the transducer may be laterally displaced along x or y direction.

The therapy transducer may operate in a range of frequencies depending on the desirable therapy. For example, the therapy transducer may operate in a frequency range from about 250 KHz to about 3 MHz, or in a range from about 500 kHz to about 1 MHz for cavitating the targeted tissues (such as diseased tissues or adipose tissues). In one example, the imaging transducer may comprise two dimensional or three dimensional array of transducer elements. The imaging transducer may operate in a range from about 1 MHz to about 15 MHz, optimally in a range from about 1 MHz to about 10 MHz, or from about 2 MHz to about 7 MHz.

The imaging transducer may image the region of interest before applying the therapy, or after applying the therapy, or while applying the therapy. In one example, the therapy transducer generates one or more ultrasound frequencies for cavitating and/or thermally treating the region of interest, and the imaging transducer may receive one or more frequencies for imaging the region of interest. The therapy transducer and/or the imaging transducer may be configured to operate in a plurality of regions of interest while maintaining the same physical location of the probe housing on the subject.

The therapy transducer may selectively operate in a low power mode or a high power mode. Correspondingly, the imaging transducer may operate in one of the two modes, an imaging mode (transmit and receive) or a receive mode (to visualize the HIFU beam). The high power mode of the therapy transducer may be used for tissue ablation. The low power mode of the therapy transducer may be used for visualizing the HIFU focus, where the therapy transducer transmits pulses in low power and the imaging transducer works as receiver. The image of the focused ultrasound may be superimposed on ultrasound images of tissue.

The controller unit 24 is used to control the delivery of therapy to the treatment locations based on one or more transducer parameters or therapy commands. Examples of a transducer parameter include, but are not limited to, a focal region depth, a focal region size, an ablation time for each point within the region of interest that receives therapy, an energy level of the therapy signals, and a rate of focal region movement within the ROI during the therapy session. The transducer parameters may also include a frequency or intensity of the therapy ultrasound signals, power, peak rare factional pressure, pulse repetition frequency and length, duty cycle, depth of field, waveform used, speed of beam movement, density of beam, therapy pulse sequence, and imaging pulse sequence parameters. Also, therapy commands may include anatomical parameters, such as the location, shape, thickness, and orientation of adipose tissue and non-adipose tissues. An anatomical parameter may also include a density of the adipose tissue and the non-adipose tissues. Furthermore, therapy parameters include the type of probe used during the therapy session. The age, gender, weight, ethnicity, genetics, or medical history of the patient may also be therapy commands. After therapy has been applied to a region of interest, the system 10 or the operator/user may adjust the therapy parameters before applying therapy to the same region of interest 12 again, or to a new region of interest. The therapy command may comprise any factor or value that may be determined by the system 10 or any input that may be entered by the user that affects the therapy applied to the region of interest. In some embodiments, the system 10 may automatically provide virtual segmentation of the differentiate tissue types. After the segmentation of the different tissue types, the location of tissues of interest for treatment may be determined. In one example, the tissues of interest may comprise fat. In another embodiment, the tissues of interest may be tumors, blood vessels, or any other tissue that needs to be destroyed (e.g., ablated). In the case of subcutaneous adipose ablation, connective tissues that may alter the HIFU may be identified, and the ablation may be modified to treat above the HIFU range of the connective tissues. Alternatively, the intensity of the HIFU may be lowered to avoid any damage to the connective tissues. In embodiments where visceral fat is to be treated, a path may be chosen so that the path allows for largest distance between the treatment region and any organs or major vessels.

The controller unit 24 may control the movement of the HIFU beam based on the identification and segmentation of the tissue types. In one example, the transducer 14 may image the region of interest to determine therapy parameters pertaining to the adipose tissue and the non-adipose tissues. The therapy parameters may be generated by the controller unit 24 and transmitted to the transmitter 18 or the beamformer 22. The controller unit 24 is configured to control the time sequence of ablation, HIFU beam imaging, tissue imaging and motion of probes. The controller unit 24 also identifies the location of the targeted tissue and the current focus of HIFU and calculates the parameters to steer the HIFU focus either mechanically or electronically. The controller unit 24 may also control the ablation parameters of a focused ultrasound during any ablation procedure.

Other parameters of the ultrasound beam that may be controlled using the controller unit 24 may include level of power, duty cycle, power time sequence for imaging of HIFU, imaging of tissue, ablation and probe movements, focal depth of the ultrasound beam. The level of power may be changed by changing the voltage setting of the ultrasound system. The duty cycle may be adjusted by adjusting one or both of the intervals and length of ultrasound pulses. The focal depth of the ultrasound beam may be adjusted by mechanically adjusting the position of the transducer relative to the region of interest.

Optionally, the system may employ a cavitation detector (not shown) to assess the amount of cavitation. Cavitation detector may be a single element or a multi-element transducer or a hydrophone. The cavitation detector may be configured to operate in a range from about 1 MHz to about 15 MHz. In one example, the elements of the imaging transducer may be used as a broadband cavitation detector. The cavitation detection may be performed by acquiring time domain (A-scan) signals and detecting broadband noise and sub-harmonics in the signal, either in time-domain or in frequency domain. Typically, higher noise is representative of the amount of cavitation. During the ablation procedure, the cavitation may be verified by the cavitation detector. The controller unit 24 may adjust the power of the transducer to maintain cavitation at minimal power or time according to a look up table and the pre-treatment input plan from the operator.

The controller unit 24 may be connected to a user interface 40, such as a mouse, keyboard, and controls operation of the probe housing. For example, the controller unit 24 may be coupled to the user interface 40 to allow a user to interface with the ultrasound system 10 based on the data displayed on the display 42, such as a monitor. The segmented ultrasound images with the HIFU beam location may be displayed using the display 42 for verification and treatment planning. The user interface may be used to accept or reject the displayed plan. For example, if the ultrasound beam is at a desirable location in the displayed image, the user may accept the treatment plan. Alternatively, if the ultrasound beam is too close to neighboring connective tissue such that the neighboring tissue may be undesirably ablated upon transmission of the ultrasound beam, the treatment plan may be either modified or rejected by the user using the user interface 40. The user interface 40 may comprise a touchscreen for the user, such as an operator, to provide inputs for treatment plans. The user interface 40 may be a touch screen, allowing the operator or user to select options by touching displayed graphics, icons, and the like.

While the threshold for muscle cavitation is significantly higher than fat tissues, it is desirous to avoid the muscle tissue as an additional safety measure against damage to the muscle tissue and subsequent pain. Viewing the segmented ultrasound images indicating the different tissue types using the display 42 enables the user to recognize that undesired tissues may be in very close proximity to skin, muscle and other organ tissues, such as the muscle and/or skin interface to the fat. Alternatively, a feedback control unit may be configured to alarm the user or the controller unit 24 to modify the treatment to avoid any undesirable effects.

The ultrasound system 10 transmits ultrasound energy to the region of interest 12 in the patient to image, and/or treat the region of interest, and receives and processes backscattered ultrasound signals from the patient to create and display an image. The ultrasound image is processed using the image processing unit 26 to identify and segment the tissue types. The image processing unit 26 then transmits command data to the controller unit 24. The controller unit 24 upon receiving command data from the image processing unit 26 facilitates generation of transmit parameters to create a beam having desired parameters, such as shape, size, depth, power and location. The transmission parameters are delivered from the controller unit 24 to the transmitter 18. The transmitter 18 uses the transmission parameters to properly encode the signals to be sent to the transducer 14 through the T/R switching circuitry 16. The signals are set at certain levels and phases with respect to each other and are transmitted to transducer element(s) of the transducer 14. The transmitted signals excite the transducer element(s) to emit ultrasound waves with the same phase and level relationships. As a result, a transmitted beam of ultrasound energy is directed at therapy site of the patient along a scan line when the transducer 14 is acoustically coupled to the therapy site of the patient by using, for example, ultrasound gel or water.

The image processing unit 26 is adapted to perform one or more processing operations according to a plurality of selectable ultrasound modalities on the acquired ultrasound information. Acquired ultrasound information may be processed in real-time during a scanning or therapy session as the echo signals are received. Additionally or alternatively, the ultrasound information may be stored temporarily in the memory 28 during a scanning session and processed in less than real-time in a live or off-line operation. In one example, the image memory 44 may be used to store processed frames of acquired ultrasound information that is not displayed immediately. The image memory 44 may comprise any known data storage medium, for example, temporary or permanent storage mediums or removable storage mediums.

Optionally, the system 10 may include a position tracking module 46 that tracks a position of the probe or the focus spot of the HIFU beam. The position-sensing device may be operatively coupled to the transducer or the probe housing to accurately determine the position of the transducer 14. The tracked position may be communicated to the other components of the system, such as the controller unit 24. The position of the probe may be tracked relative to a reference point/landmark on or near the patient, a marker, and the like. In one example, the position of the probe may be used to indicate, to the user, regions of the patient that have already been treated, are being treated, or are yet to be treated.

After or while providing therapy to an area within the region of interest 28, the user or the system 10 may determine, whether the therapy is complete for the region of interest 28 and if the focus spot of the ultrasonic beam should be moved to another point within the patient. Automatic determination of whether the treatment space has been sufficiently treated or completed may be determined by methods, such as but not limited to, elasto-graphic methods. Alternatively, the user or a feedback module 48 may determine whether the therapy is complete. The feedback module 48 may also be linked to the position tracking module 46 to determine whether the focus spot is at the desired position. The feedback module 48 may be coupled to the controller unit 24 or the image processing unit 26. In addition, although not illustrated, the feedback module 48 may also be coupled to one or more of the display 42, memory 28, image memory 44, and the user interface 40. The feedback module 48 may compare the actual output of the system with the desired output. The actual output refers to the result of the therapy delivered to the region of interest. The actual output may be provided as displayed images, or images stored in the memory 28 or 44, or the data related to the displayed or stored images. The desired output may be specified by the user. For example, the desired output may be specified by the user depending on the amount of tissue to be treated.

The feedback module 48 may compare the actual output and the desired output and inform/alert the system 10 if required. In case of fat reduction, the feedback module 48 may use the therapy commands provided to the system 10 by the user to determine the acceptable levels of adipose tissue reduction and thermal treatment, and accordingly notify the system when such limits are exceeded or approaching. In one example, the feedback module 48 may alert the system by beeping or flashing a signal on the monitor, to caution the user, for example, if the determined limit of adipose tissue to be cavitated exceeds or is about to reach closer to the boundary denoted by segmentation. In one embodiment, the feedback module 48 may have built-in intelligence that may alter the therapy parameters to amend the therapy being provided.

The feedback module 48 may take the data from the processing unit 26, displayed images (on the display 42), or memories 28 or 44 images, as the input and make a decision whether the data or images are acceptable. For example, the feedback module 48 may use the displayed images to determine whether the amount of adipose tissue cavitated in the region of interest 12 is sufficient to stop the therapy in the region of interest 12. The feedback module 48 may either provide feedback after completion of the therapy, or during the therapy. In one example, the feedback module 48 may verify whether the amount of the adipose tissue reduced from a given portion is acceptable by comparing the actual amount of the adipose tissue cavitated with the adipose tissue value calculated using the therapy parameters. If, for example, the depth of the adipose tissue ablated exceeds, or is about to exceed a determined value, the feedback module 48 may be configured to raise an alarm, such as a continuous beep, till the user acknowledges receiving the beep (for example by means of the user interface 40). The user may then review the information from the feedback module 48. In this manner, the feedback module 48 may avoid inadvertent user errors that could otherwise occur.

The controller unit 24, the image processing unit 26, and other modules and units of the system 10 may be implemented utilizing an off-the-shelf PC with a single processor or multiple processors, with the functional operations distributed between the processors. The components may be dedicated hardware elements such as circuit boards with digital signal processors or may be software running on a general-purpose computer or processor such as a commercial, off-the-shelf personal computer (PC). The various components may be combined or separated according to various embodiments of the invention. The ultrasound system 10 is an example, and the systems and methods of the invention are not limited by this specific system configuration.

Figure 2:
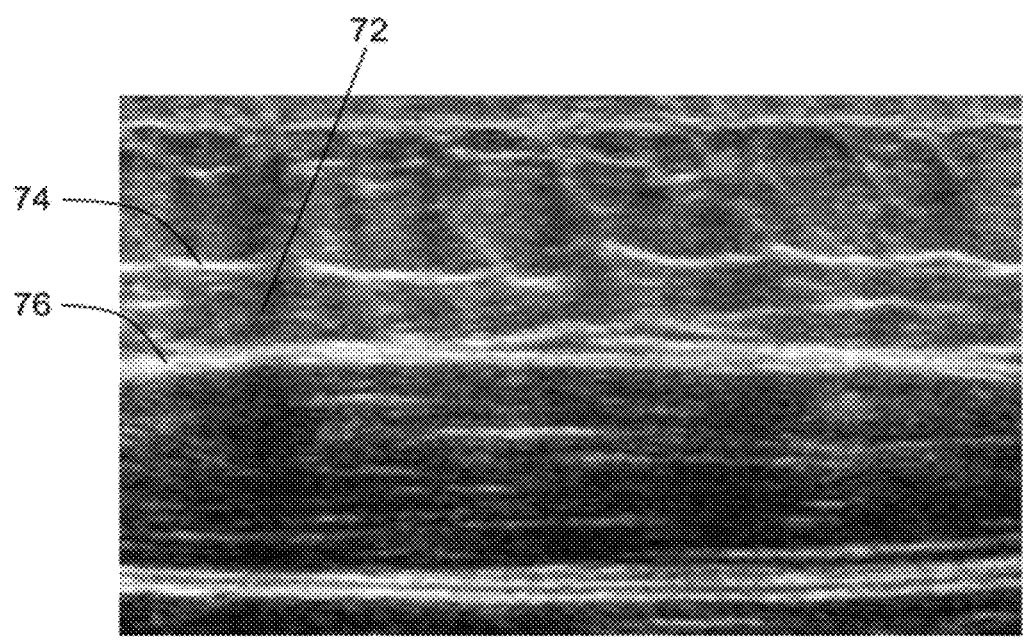
FIG. 2 is an example ultrasound image indicating different tissue types comprising fat and connective tissues.

In one example, the fat layer may be automatically identified and segmented by the ultrasound system of the invention. In one example, the fat layer in the ultrasound images for tissue in abdominal region may be automatically identified and segmented. FIG. 2 illustrates an ultrasound image of tissue from the abdominal region in which the various cellular layers have been identified. The fat layer 72 is wedged between two layers 74 and 76 of fibrous connective tissue. In one embodiment, the tissue types may be identified based on texture and/or mean intensity values of the tissues. The fat layer, in most instances, has a characteristic texture defined by sparsely distributed diagonal striations. In certain embodiments, this physiologic manifestation may be utilized in developing an automated image processing algorithm for delineating the fatty layer in ultrasound images.

Figure 3:
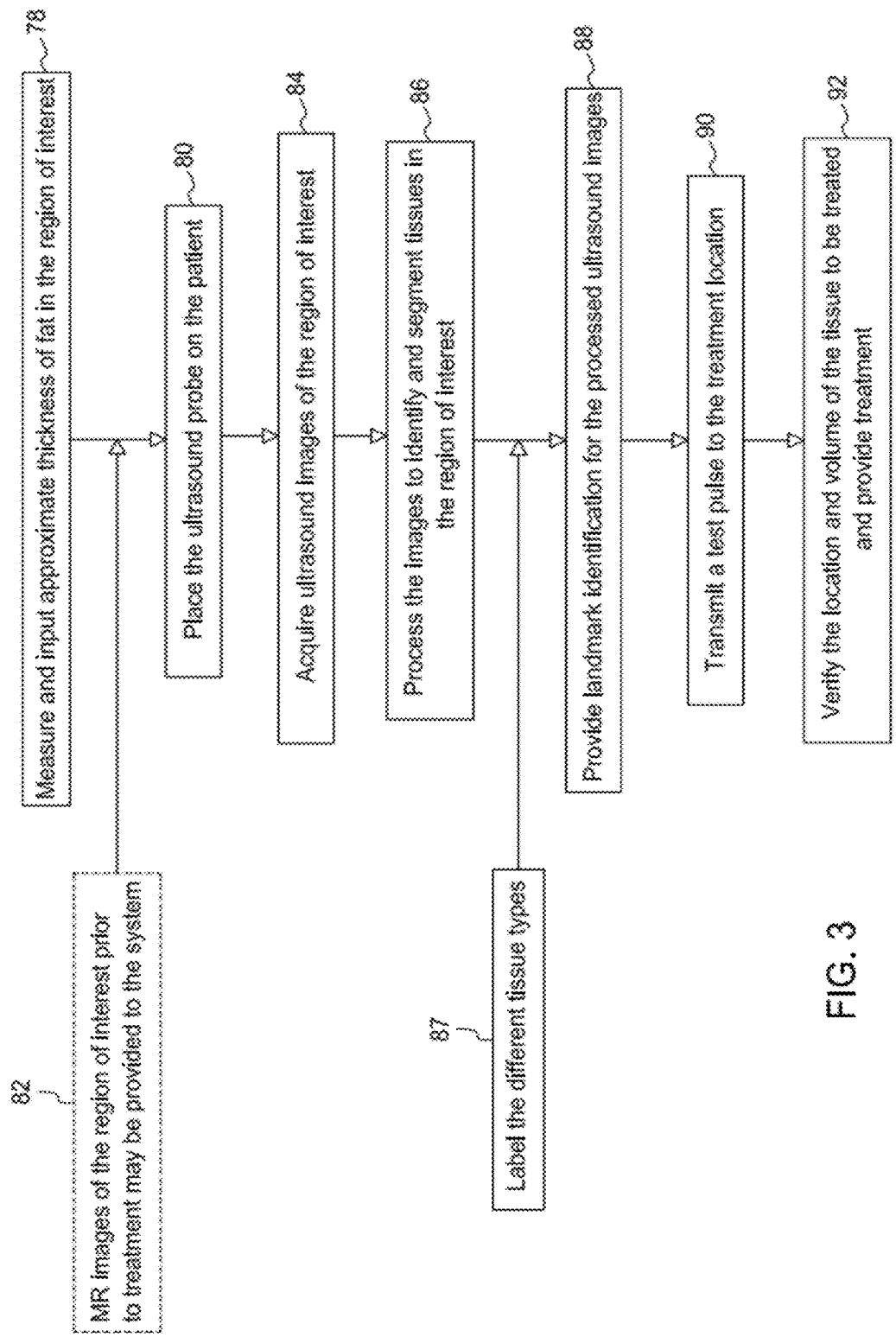
FIG. 3 is a flow chart for an example method for automatically identifying and segmenting tissue types in a region of interest.

FIG. 3 is a flow chart for an example method for automatically identifying and segmenting tissue types in an ultrasound image. At step 80, the method commences by placing the ultrasound probe on the patient. Optionally, prior to step 80, at step 78, the physician or the technician may measure and input approximate thickness of fat in the region of interest. Also, optionally, as a pre-procedure step, at step 82, magnetic resonance (MR), X-ray, computed tomography (CT), or dual energy X-ray (DXA) images of the region of interest may be provided to the system prior to treatment. These MR, X-ray, CT or DXA images may be used as a reference to compare images obtained by the ultrasound system at subsequent stages during the procedure. Along with the pre-procedure images, user may provide information relating to the region of interest to the system. For example, the information provided by the user may comprise basic information regarding the patient, and the location of the region of interest in the patient, and the types of tissues present in the region of interest. In one example, the user may input information that the area being imaged is abdominal and that a human abdomen has a layer of skin, fat and muscle, in that order.

At step 84, the system acquires ultrasound images of the region of interest. The images of fat and muscle border may be acquired by an integrated probe, also referred to as a dual use probe that may comprise a HIFU probe and an imaging probe. Alternatively, a separate ultrasound imaging probe may be used to acquire the images.

At step 86, after determining the location for providing treatment but prior to providing the treatment, the images are processed by the signal processing software. In one example, the image processing unit may comprise the signal processing software. The signal processing software may use one or more algorithms for carrying out analysis of the image data to find the boundaries of the tissues (fat, muscle, connective tissues etc.). Different tissue types, such as fat, connective tissue and muscle in the acquired ultrasound images may be automatically identified and segmented using the algorithms. In one example, based on the landmarks and known tissue structures the different tissue types may be identified. Optionally, the identified and segmented tissue portions may be labeled to indicate the tissue type present in the different segments of the processed images (step 87). The landmarks may be based on prior knowledge of the tissue types. In one example, the prior knowledge may be incorporated through a learning framework comprising a set of training images in which the various tissue types are indicated through manual markings by a user, e.g., a trained clinician. The features pertinent to each tissue type may then be learnt from these training images using any of the available learning methods, such as but not limited to, probabilistic boosting tree.

For fat reduction procedures, location of fat may be determined in the segmented ultrasound image. In case of other treatments, locations of corresponding tissues, such as tumors, blood vessels, that are to be treated may be determined in the segmented ultrasound image.

At step 88, the processed ultrasound images may be sent to the treatment verification software with landmark identification and displayed. A comprehensive map of the tissue structure in the region of structure having landmark identification may be displayed. The displayed image may illustrate different tissue types that are identified and segmented. The displayed image generated by the system may comprise a labeled image showing the various tissue layers along with their corresponding thickness measurements. Optionally, the displayed image having the identification of tissues may also comprise identification of the HIFU focal spot location. This displayed image may be shown to the user with the additional option of operator adjustment.

At step 90, a test pulse may be created by the HIFU and received by the imaging transducer. This image of HIFU beam may be displayed with the processed image. At step 92, the location and volume of the tissues to be treated may be verified by the user. A preliminary treatment plan may be calculated based on the volume of tissues to be treated, tissues quality and location and desired procedure time. In case of subcutaneous adipose ablation, connective tissues that may alter the HIFU may be identified and the ablation treatment may be accordingly modified to treat above (or below) the connective tissues to avoid the treatment being delivered to the connective tissues. While treating visceral fat, a treatment path may be chosen so that maximum possible distance may be allowed between the treatment region and any organs or major vessels.

Based on the segmentation, the ablation may be planned and the focus of the HIFU may be adjusted accordingly to treat the region of interest. The focus of the HIFU may be adjusted by inflating or deflating a standoff between the patient and the transducer, using a phased array electronically steering the HIFU or mechanical motion of the transducer. In one example, HIFU may be pulsed briefly at low energy and the HIFU may be imaged with the imaging transducer. In this example, the imaging transducer and the therapy transducer may be at the same frequency or harmonics. After providing the treatment the region of interest may be imaged to determine the amount of treatment delivered, and a decision may be made by the system or the user to continue or stop the treatment. During the procedure, the position of the probe providing the treatment may be tracked either by optical, EM, gyroscopic tracking or via mechanical means of robotics or rails.

The algorithm for identification of tissue types, such as identification of fat layers 94 and connective tissue layers 96, in ultrasound images may be employed to provide segmentation. The first step in the algorithm may comprise detecting the connective tissue layers. Prior to detecting the connective tissue layers, an image enhancement procedure may be performed. The input ultrasound image may be enhanced using a connective tissue enhancing filter configured to segment the connective tissues. The connective tissue enhancing filter is utilized to enhance ridge-like image features in the ultrasound image, which highlight the connective tissue layers in the ultrasound image. This enhanced image may be presented to the user (e.g., clinician) for enhanced visualization of the various tissue layers. The connective tissue enhancing filter may employ a Hessian based measure for enhancement of tubular structures (connective tissue layers) in the image. For an image, I, the Hessian H is defined, using the $2^{nd}$ order partial derivatives, as:

$$H = \begin{bmatrix} \frac{\partial^2 I}{\partial x^2} & \frac{\partial^2 I}{\partial x \partial y} \\ \frac{\partial^2 I}{\partial x \partial y} & \frac{\partial^2 I}{\partial y^2} \end{bmatrix} = \begin{bmatrix} I_{xx} & I_{xy} \\ I_{xy} & I_{yy} \end{bmatrix} \quad \text{Equation 1}$$

By extracting the eigenvalues of the Hessian, the principal directions of the local second order structure are decomposed. If the eigenvalues of this Hessian matrix are represented as $\lambda_1$ & $\lambda_2$. Then, for an ideal tubular structure on a 2D image Equation 2 needs to be satisfied.

$$|\lambda_1| \approx 0 \, \& \, |\lambda_1| << |\lambda_2| \quad \text{Equation 2}$$

The 2D vesselness measure may be defined at a scale s as represented in Equation 3.

$$V(s) = \{0, (e^{-(|\lambda_1|/|\lambda_2|)^2/2\beta^2})(1 - e^{-(\lambda_1^2 + \lambda_2^2)/2c^2})\} \text{ if } \lambda_2 > 0$$

where, $\beta$ is a factor that accounts for deviation from a blob-like structure. The factor c, allows for exclusion of noise pixels, as these typically have equal eigenvalues. The connective tissue enhanced image is generated at multiple scales and the results summed up to generate the final image. An example of the corresponding connective tissue enhanced image for the input image of FIG. 4 is depicted in FIG. 5. As illustrated, coarse segmentation of the connective tissue layers is provided by enhancement filter.

Next, the connective tissue layers may be segmented from the enhanced image using a scheme that comprises a thresholding process followed by a curve evolution incorporated into an active contours framework. The connective tissue layers are segmented using an active contours approach. An active contours approach is suitable for connective tissue layer segmentation as the technique is capable of tiding over minor boundary discontinuities and also adapt to varying topology. However, active contour models are sensitive to contour initialization and a good initialization is necessary for final convergence. In certain embodiments, the segmentation is implemented as a two-step process with the first step comprising of determining the active contour initialization and the second step comprising the propagation of this contour to capture the connective tissue boundary. A detailed description of each of the two steps is described below.

For contour initialization an approximate location of the connective tissue layer may be obtained by segmenting the vessel-enhanced image using a k-means intensity thresholding procedure. Since the connective tissue layer in general has a much higher intensity than its surroundings, it is easily visualized in the segmented image. However, this segmentation is only approximate as the detected region might have several discontinuities due to inhomogeneity in the connective tissue layer and/or due to presence of other imaging artifacts. As illustrated in FIG. 6, subsequent to segmentation, the boundaries of the segmented connective tissue layer are utilized to initialize the active contours. The contour pairs (in curly braces 97) are initialized above and below the detected connective tissue layers.

Figure 10:
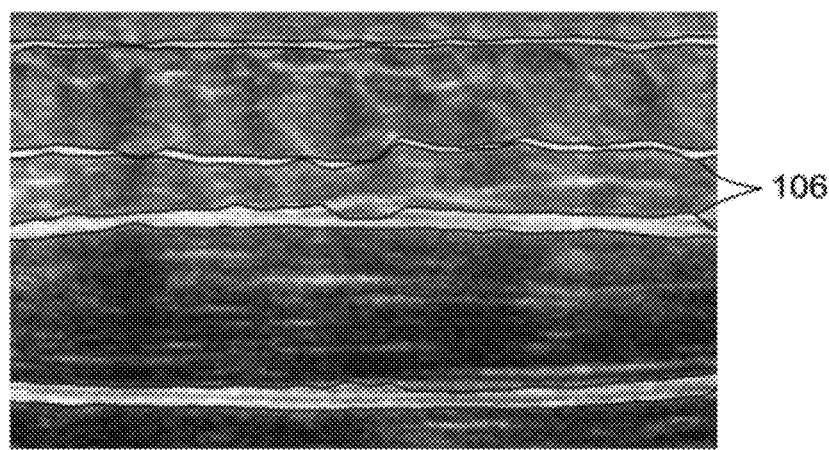

For contour propagation based on an active contours framework the boundary of the connective tissue layer may be obtained through minimization of the energy functional defined by Equation 4 as represented below:

$$E(f, g, \mu_1, \mu_2, \mu_3) = \int_a^b \int_f^g (I - \mu_1)^2 + \quad \text{Equation 4}$$

$$\int_a^b \int_0^f (I - \mu_2)^2 + \int_a^b \int_g^\infty (I - \mu_3)^2 \int_a^b \int_g^\infty (I - \mu_3)^2 +$$

$$\lambda_{smooth} \int_a^b \sqrt{1 + (f')^2} +$$

$$\lambda_{smooth} \int_a^b \sqrt{1 + (g')^2} + \lambda_{width} \int_a^b (w - (f - g))^2$$

where, f and g are the propagating contours, $\mu_1$, $\mu_2$, and $\mu_3$ are the mean intensities for regions 1, 2 and 3 respectively, $\lambda_{smooth}$ is a parameter controlling the smoothness of the evolving contour, w is an estimate of the connective tissue layer width and $\lambda_{width}$ is a penalty factor for preventing the contours from diverging away or collapsing onto each other. Equations 5-6 represent the Mumford-Shah functional and may be minimized through the iterative gradient descent approach as follows:

$$f^{(n+1)} = f^{(n)} - \lambda_{speed} * dT \left[ (I - \mu_2)^2 - (I - \mu_1)^2 - \lambda_{smooth} \left( \frac{f'}{\sqrt{1+(f')^2}} \right)' - \lambda_{width}(w-(f-g)) \right] \qquad \text{Equation 5}$$

$$g^{(n+1)} = g^{(n)} - \lambda_{speed} * dT \left[ (I - \mu_1)^2 - (I - \mu_3)^3 - \lambda_{smooth} \left( \frac{g'}{\sqrt{1+(g')^2}} \right)' + \lambda_{width}(w-(f-g)) \right]. \qquad \text{Equation 6}$$

where, the superscript (n) references the iteration and $\lambda_{speed}$ is a term controlling the propagation speed. It is desirable to set $\lambda_{speed}$ to be inversely proportional to the normalized image intensity so as to speed up the contour evolution in regions where the connective tissue layer is absent and to slow it down when the contours approaches the connective tissue layer. The iterative scheme in Equation 5 is continued till either the maximum number of iterations (~2000) is reached or the contours do not change significantly from one iteration to the next. FIGS. 7, 8 and 9 illustrate contour evolution with the progressing iterations. FIG. 7 illustrates fat tissue layer 98 and connective tissue layer 100 in the initial ultrasound image of the region of interest, and FIGS. 8 and 9 presents an example depicting the evolution of the contour over several iterations. FIGS. 8 and 9 illustrate evolution of contours 102 and 104 after 300 and 600 iterations, respectively. FIGS. 8 and 9 are intermediate steps of image processing and may or may not be displayed to the operator. The procedure or iterations are repeated until all the connective tissue layers in the image have been identified. FIG. 10 illustrates final contour 106 achieved after the total number of iterations. The lines represented by reference numerals 106 depict the active contours that have converged onto the connective tissue layer boundary.

In the final step, a novel wavelet-based texture identification scheme is implemented to classify each region between the connective tissues into one of several classes (e.g.: fat, muscle, abdominal fluid, etc.). The final result generated by the automated algorithm may comprise a labeled image showing the various tissue layers along with their corresponding thickness measurements. Optionally, the final image having the identification of tissues may also comprise identification of the HIFU focal spot location. This final image may be shown to the operator with the additional option of operator adjustment.

In the next step the regions lying between all the connective tissue layers are identified and the region most distal to the skin is classified as muscle. All other regions, which have a mean intensity significantly greater than muscle, are classified as fat.

Figure 11:
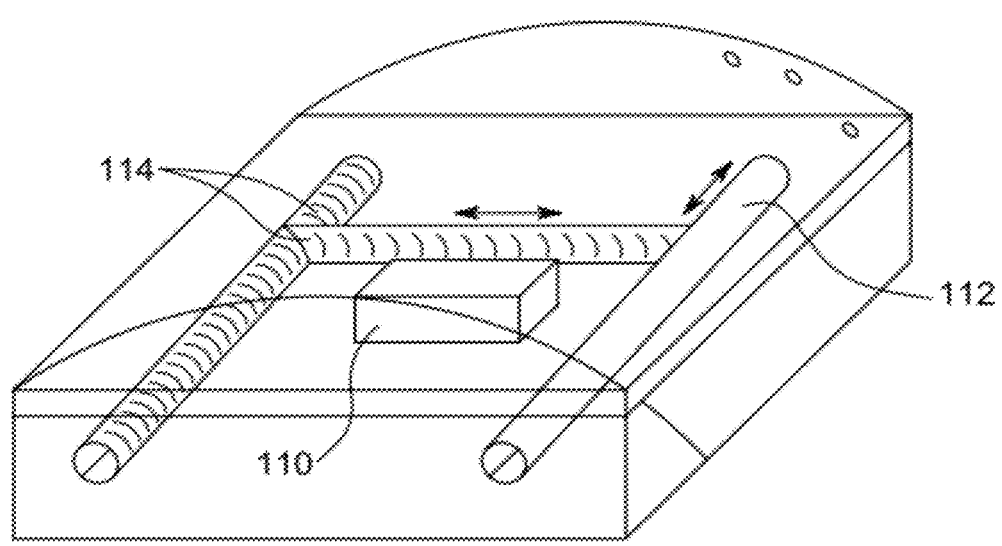
FIG. 11 is a schematic drawing of an example set up for moving a single element transducer on a patient.

FIG. 11 illustrates an arrangement for a single element HIFU transducer 110 for providing adjustment for the depth and location of the HIFU beam by mechanical adjustment of the distance/location of the transducer 110 relative to the skin. The transducer 110 is configured to be moved with reference to a frame 112. The frame may be defined using a pair of rails 114 that are spatially separated and extend along y-axis of the frame 112. The transducer 110 is slidably mounted on the rails 114, for example, in tracks (not shown). The frame 112 may be substantially flat or contoured similar to a corresponding region of a patient's body (also not shown). The transducer 110 may be moved along the rails while remaining substantially constantly in contact with the patient's body. The frame 112 may either allow manual or motorized movement of the transducer with respect to the patient's body.

Figure 12:
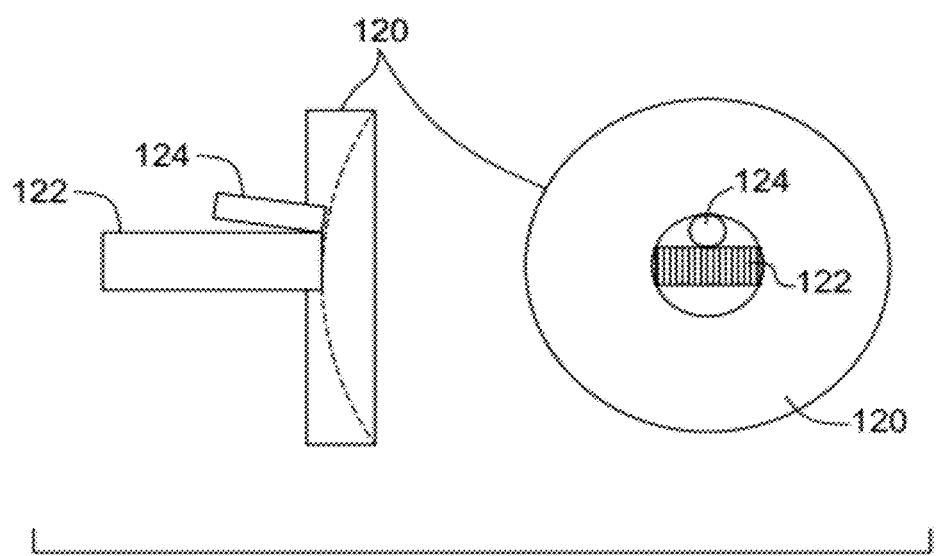
FIG. 12 is a schematic drawing of an example integrated transducer comprising a phased array, an imaging transducer and a cavitation detector.

FIG. 12 illustrates a multi-element HIFU array 120 having a plurality of transducer elements. The transducer array 120 is an annular array. An adjustment in focal spot location may be made with an adjustment of the individual radio frequency amplifiers that control the individual transducer elements. An imaging transducer 122 and a cavitation detector 124 are disposed in operative associated with the transducer array 120. The array 120 may be configured for adjusting depth of the HIFU focal spot. A lateral motion of the array 120, and hence the focal spot, may be with an adjustment of the radio frequency amplifier control coupled to the radio frequency amplifiers of the individual transducer elements.

EXAMPLE

Four volunteers were subjected to an ultrasound scan in the abdominal region using a linear array probe and the depth was adjusted such that the entire fat layer was captured in the field of view. The images were then analyzed using the proposed automated algorithm and the results were qualitatively examined to determine segmentation accuracy. The algorithm was able to correctly identify the connective tissue layers in all of the images. However, the classification of regions into fat and muscle was not always accurate owing to a rather small intensity difference observed between the two layers in several cases. An automated algorithm for fatty layer detection in ultrasound images of abdominal tissue was used. The algorithm utilizes an active contours framework for connective tissue layer segmentation followed by intensity binning to classify the regions between the connective layers as either fat or muscle. The algorithm was tested on ultrasound images from sixteen volunteers and the results indicate good segmentation accuracy of the connective tissue layers. However, the intensity difference between the fat and muscle regions was not always significant leading to a few misclassifications. A more robust classification scheme to differentiate between fat and muscle may be obtained by studying the textural properties of the two layers. The fatty layer has predominantly diagonal striations, while the muscle layer exhibits sparsely distributed horizontal striations. Future work involves utilizing this information in a texture classification framework to better differentiate between the two categories.

Figure 13:
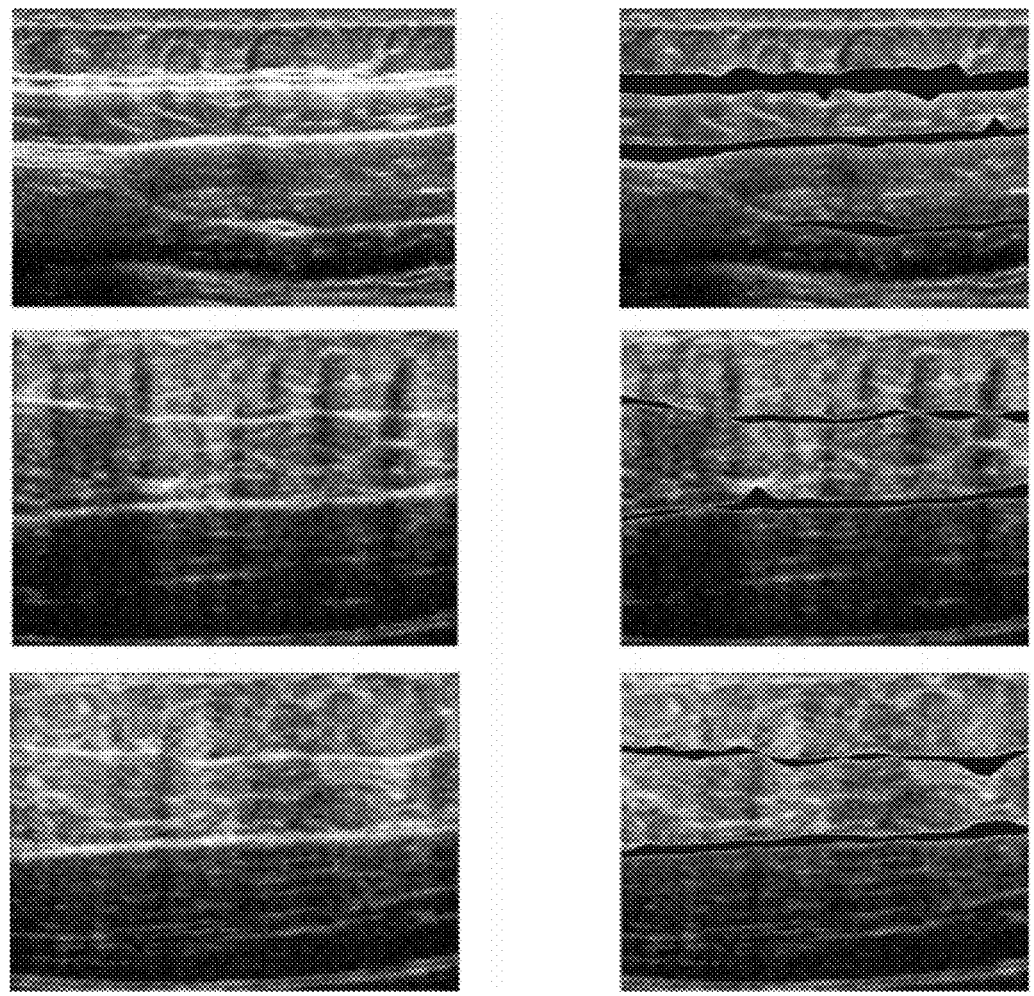
FIG. 13 are examples of input ultrasound images vs. processed images after applying methods of the invention to the input ultrasound images for automatically identifying and segmenting tissue types in corresponding regions of interest.

The algorithm has been tested on a set of sixteen images from different volunteers and a qualitative examination of the results indicates good segmentation accuracy. FIG. 13 illustrates input image and the corresponding segmentation generated using the automated algorithm, wherein the connective tissue layers and the fat/muscle regions have been identified using the automated algorithm.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A system for providing non-invasive ultrasound based treatment to a region of interest, the system comprising:
    an imaging transducer configured to acquire an ultrasound image of two or more tissue types in the region of interest;
    an image processing unit coupled to the imaging transducer and configured to identify and segment the two or more tissue types in the region of interest;
    a therapy transducer configured to focus an ultrasound beam to ablate at least a portion of the identified tissues, wherein the therapy transducer is configured to undergo a mechanical adjustment of a distance or a location to provide an adjustment for a depth, a location, or both the depth and the location of the ultrasound beam in the region of interest; and
    a controller unit coupled to the image processing unit and the therapy transducer, wherein the controller unit is configured to receive processed data from the image processing unit and control the therapy transducer to control a delivery of the ultrasound beam to the region of interest based on the identification and segmentation of the two or more tissue types.

2. The system of claim 1, wherein the imaging transducer operates in a frequency range of about 1 MHz to about 15 MHz.

3. The system of claim 1, further comprising a cavitation detector.

4. The system of claim 3, wherein the imaging transducer comprises the cavitation detector.

5. The system of claim 3, wherein the cavitation detector is configured to operate in a range from about 1 MHz to about 15 MHz.

6. The system of claim 1, wherein the therapy transducer is configured to operate in a range from about 250 KHz to about 3 MHz.

7. The system of claim 1, further comprising a feedback module coupled to the image processing unit or the controller unit.

8. The system of claim 1, wherein the image processing unit comprises a connective tissue enhancing filter configured to segment connective tissues.

9. The system of claim 1, wherein the therapy transducer is a high intensity focused ultrasound (HIFU) transducer.

10. The system of claim 1, wherein the therapy transducer comprises a single element.

11. The system of claim 1, wherein the therapy transducer comprises a phased array, or an annular array of transducer elements.

12. The system of claim 1, further comprising a position tracking module configured to track a position of the focus of the ultrasound beam, wherein the position tracking module is coupled to the controller unit.

13. The system of claim 1, wherein the image processing unit comprises a tissue atlas.

14. A method for treating a region of interest using ultrasound, comprising:
    acquiring ultrasound images of the region of interest;
    identifying two or more tissue types in the ultrasound images by detecting connective tissue layers based on landmarks and known tissue structures;
    segmenting the two or more tissue types in the ultrasound images, wherein the step of segmenting comprises:
        determining an active contour initialization;
        propagating the active contour to capture a connective tissue boundary;
    identifying tissues to be ablated based on the segmentation of the two or more tissue types;
    focusing an ultrasound beam to ablate at least a portion of the identified tissues; and
    ablating at least the portion of the identified tissues.

15. The method of claim 14, further comprising adjusting a focus of the ultrasound beam to a determined portion of the identified tissues.

16. The method of claim 14, further comprising modifying an energy of the ultrasound beam based in part on tissue identification.

17. The method of claim 14, wherein the two or more tissue types comprise fat tissues, muscle tissues, or connective tissues.

18. The method of claim 14, further comprising labeling the identified tissues.

19. The method of claim 14, wherein focusing the ultrasound beam to ablate at least the portion of the identified tissues comprises delivering the ultrasound beam in a pulsed form.

20. The method of claim 14, further comprising intermittently imaging the portion of the identified tissues during ablation.

21. The method of claim 14, wherein identifying the two or more tissue types in the region of interest comprises identifying textures or mean intensities of the two or more tissue types.

22. The method of claim 14, wherein the step of determining the active contour initialization comprises determining an approximate location of a connective tissue layer by segmenting a vessel-enhanced image.

* * * * *